US00PP26468P2

(12) United States Plant Patent
Koppe

(10) Patent No.: US PP26,468 P2
(45) Date of Patent: Mar. 8, 2016

(54) ***BEGONIA* PLANT NAMED 'KROUTOR01'**

(50) Latin Name: ***Begonia boliviensis*×*Begonia*×*tuberhybrida***
Varietal Denomination: KROUTOR01

(71) Applicant: Lubbertus H. Koppe, Putten (NL)

(72) Inventor: Lubbertus H. Koppe, Putten (NL)

(73) Assignee: Koppe Royalty B.V., Putten (NL)

( * ) Notice: Subject to any disclaimer, the term of this patent is extended or adjusted under 35 U.S.C. 154(b) by 207 days.

(21) Appl. No.: 13/998,905

(22) Filed: Dec. 19, 2013

(51) Int. Cl.
*A01H 5/02* (2006.01)

(52) U.S. Cl.
USPC ..... Plt./343

(58) Field of Classification Search
USPC ..... Plt./347, 343
See application file for complete search history.

*Primary Examiner* — Anne Grunberg
(74) *Attorney, Agent, or Firm* — C. A. Whealy

(57) ABSTRACT

A new and distinct cultivar of *Begonia* plant named 'KROUTOR01', characterized by its upright to broadly spreading and mounded plant habit; freely basal branching habit; dark green-colored leaves; large single-type dark orange-colored flowers; and excellent garden performance.

2 Drawing Sheets

Botanical designation: *Begonia boliviensis*×*Begonia*×*tuberhybrida.*

Cultivar denomination: 'KROUTOR01'.

BACKGROUND OF THE INVENTION

The present invention relates to a new and distinct cultivar of *Begonia* plant, botanically known as *Begonia boliviensis*×*Begonia*×*tuberhybrida* and hereinafter referred to by the name 'KROUTOR01'.

The new *Begonia* plant is a product of a planned breeding program conducted by the Inventor in Ermelo, The Netherlands. The objective of the breeding program is to create new *Begonia* plants with excellent outdoor performance.

The new *Begonia* plant originated from a cross-pollination made by the Inventor in Ermelo, The Netherlands in March, 2006 of *Begonia boliviensis* 'Bonfire', disclosed in U.S. Plant Pat. No. 15,108, as the female, or seed, parent with a proprietary selection of *Begonia*×*tuberhybrida* identified as code number KV02K0352-013, not patented, as the male, or pollen, parent. The new *Begonia* plant was discovered and selected by the Inventor as a single flowering plant from within the progeny of the stated cross-pollination in a controlled greenhouse environment in Ermelo, The Netherlands in February, 2007.

Asexual reproduction of the new *Begonia* plant by cuttings taken in a controlled greenhouse environment in Ermelo, The Netherlands since July, 2007 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'KROUTOR01'. These characteristics in combination distinguish 'KROUTOR01' as a new and distinct *Begonia* plant:

1. Upright to broadly spreading and mounded plant habit.
2. Freely basal branching habit.
3. Dark green-colored leaves.
4. Large single-type dark orange-colored flowers.
5. Excellent garden performance.

Plants of the new *Begonia* differ primarily from plants of the female parent, 'Bonfire', in the following characteristics:

1. Plants of the new *Begonia* are more upright than and not as pendulous as plants of 'Bonfire'.
2. Plants of the new *Begonia* have larger leaves than plants of 'Bonfire'.
3. Plants of the new *Begonia* have larger flowers than plants of 'Bonfire'.

Plants of the new *Begonia* differ primarily from plants of the male parent selection in flower form as plants of the male parent selection have semi-double flowers. In addition, plants of the new *Begonia* have narrower leaves than plants of the male parent selection.

Plants of the new *Begonia* can be compared to plants of *Begonia*×*tuberhybrida* 'Sunjiraore', disclosed in U.S. Plant Pat. No. 24,266. In side-by-side comparisons conducted in Ermelo, The Netherlands, plants of the new *Begonia* differed primarily from plants of 'Sunjiraore' in leaf and flower size as plants of the new *Begonia* had larger leaves and flowers than plants of 'Sunjiraore'.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet comprises a side perspective view of a typical plant of 'KROUTOR01' grown in a container.

The photograph on the second sheet is a close up view of typical flowers and leaves of 'KROUTOR01'.

DETAILED BOTANICAL DESCRIPTION

The aforementioned photographs and following observations and measurements describe plants grown during the autumn in 13-cm containers in a glass-covered greenhouse in Ermelo, The Netherlands and under cultural practices typical of commercial *Begonia* production. During the production of the plants, day temperatures averaged 19° C. and night temperatures averaged 18° C. Plants were twelve weeks old when the photographs and description were taken. In the following description, color references are made to The Royal Horticultural Society Colour Chart, 2007 Edition, except where general terms of ordinary dictionary significance are used.

Botanical classification: *Begonia boliviensis*×*Begonia*×*tuberhybrida* 'KROUTOR01'.

Parentage:

*Female, or seed, parent*.—*Begonia boliviensis* 'Bonfire', disclosed in U.S. Plant Pat. No. 15,108.

*Male, or pollen, parent*.—Proprietary selection of *Begonia*×*tuberhybrida* identified as code number KV02K0352-013, not patented.

Propagation:

*Type*.—By cuttings.

*Time to initiate roots, summer and winter*.—About 20 days at temperatures about 19° C.

*Time to produce a rooted young plant, summer and winter*.—About five weeks at temperatures about 19° C.

*Root description*.—Fine, fibrous; white to orange brown in color.

*Rooting habit*.—Freely branching; medium density; plants of the new *Begonia* have not been observed to form tubers.

Plant description:

*Plant habit and form*.—Upright to broadly spreading and mounded plant habit.

*Growth habit*.—Moderately vigorous growth habit and moderate growth rate; suitable for 12-cm and larger containers; under optimal environmental and cultural conditions, usually about twelve weeks are required to produce proportional 13-cm potted plants from cuttings.

*Branching habit*.—Freely basal branching habit, about eleven basal branches develop per plant; dense and bushy habit.

*Plant height*.—About 26.7 cm.

*Plant width*.—About 40.2 cm.

*Lateral branches*.—Length: About 14.1 cm. Diameter: About 8 mm. Internode length: About 3.1 cm. Aspect: Erect to about 50° from vertical. Strength: Flexible, bending with the weight of the flowers. Texture: Moderately pubescent. Color, developing: Close to 152A. Color, developed: Close to N199A.

*Leaves*.—Arrangement: Alternate; simple. Length: About 14.5 cm. Width: About 6.1 cm. Shape: Unequally ovate. Apex: Acuminate. Base: Oblique. Margin: Biserrate. Texture, upper surface: Sparsely pubescent; velvety. Texture, lower surface: Moderately pubescent, especially along the veins. Luster, upper surface: Moderately glossy. Luster, lower surface: Slightly glossy. Venation pattern: Pinnate. Color: Developing leaves, upper surface: Between 138A and 143A. Developing leaves, lower surface: Close to 138B. Fully expanded leaves, upper surface: Darker than N189A; venation, close to 143A. Fully expanded leaves, lower surface: Close to 191A; venation, close to 148A. Petioles: Length: About 4.2 cm. Diameter: About 4 mm. Texture, upper and lower surfaces: Sparsely to moderately pubescent. Color, upper surface: Between 165A and 177B; distal end tinged with close to 185A. Stipules: Two present at the base of the leaf. Length: About 8 mm. Width: About 7 mm. Shape: Broadly ovate. Color, upper and lower surfaces: Close to 154C to 154D; venation, close to 179A.

Flower description:

*Flower form and flowering habit*.—Large single-type rotate flowers arranged in axillary compound cymes; usually about three female flowers and two male flowers per cyme, numerous cymes in flower simultaneously and about 275 flowers developing per plant; flowers face outwardly to slightly drooping and positioned above and beyond the foliar plane.

*Natural flowering season*.—Plants begin flowering about five weeks after pinching; plants flower naturally from the spring to autumn in The Netherlands.

*Flower longevity*.—Individual flowers last about two weeks on the plant; flowers not persistent.

*Fragrance*.—None detected.

*Inflorescence height*.—About 6.8 cm.

*Inflorescence diameter*.—About 10.8 cm.

*Female flowers*.—Flower buds: Length: About 2.8 cm. Diameter: Ranging from about 7 mm to 18 mm. Shape: Broadly ovate, flattened. Color: Close to 35B. Flowers: Diameter: About 6.3 cm. Depth: About 4 cm. Shape: Rotate. Tepals: Quantity per flower: About five to seven arranged in a single whorl. Length: About 3.9 cm. Width: About 3.2 cm. Shape: Obovate. Apex: Rounded. Margin: Entire. Texture, upper surface: Smooth, glabrous; velvety. Texture, lower surface: Smooth, glabrous. Color: When opening, upper surface: Close to 40A. When opening, lower surface: Close to 41A; towards the base, close to 41B to 41C. Fully opened, upper surface: Close to 40A; towards the base, close to 40B; color does not fade with development. Fully opened, lower surface: Close to 40A; color does not fade with development. Tepaloids: None observed on female flowers. Pedicels: Length: About 4.1 cm. Diameter: About 2 mm. Angle: About 45° from peduncle axis. Strength: Flexible, bending with the weight of the flowers. Texture: Sparsely pubescent. Color: Close to 146C or close to 42B to 42D.

*Male flowers*.—Flower buds: Length: About 2.5 cm. Diameter: Ranging from about 8 mm to 24 mm. Shape: Broadly ovate, flattened. Color: Close to 40C to 40D. Flowers: Diameter: About 7.7 cm. Depth: About 2.5 cm. Shape: Cruciform, four-parted. Tepals: Quantity per flower: About four arranged in a single whorl. Length: About 4.6 cm to 4.7 cm. Width: About 3.4 cm to 4.3 cm. Shape: Two tepals, obovate and two tepals, orbicular to reniform. Apex: Rounded. Margin: Entire. Texture, upper surface: Smooth, glabrous; velvety. Texture, lower surface: Smooth, glabrous.

Color: When opening, upper surface: Close to 33A. When opening, lower surface: Close to 40B; towards the base, close to 40C. Fully opened, upper surface: Close to between 33A and 40A; color does not fade with development. Fully opened, lower surface: Close to 40B; color does not fade with development. Tepaloids: Quantity per flower: If present, up to three arranged in a single whorl. Length: About 2.5 cm. Width: About 1.4 cm. Shape: Falcate-obovate to obovate. Apex: Rounded. Margin: Entire. Texture, upper surface: Smooth, glabrous; velvety. Texture, lower surface: Smooth, glabrous. Color: When opening, upper surface: Close to 33A. When opening, lower surface: Close to 40B; towards the base, close to 40C. Fully opened, upper surface: Close to between 33A and 40A; color does not fade with development. Fully opened, lower surface: Close to 40B; color does not fade with development. Pedicels: Length: About 2.1 cm. Diameter: About 2 mm. Angle: Upright to about 45° from peduncle axis. Strength: Flexible, bending with the weight of the flowers. Texture: Sparsely pubescent. Color: Close to 146C or close to 42B to 42D.

*Peduncles*.—Length: About 6.5 cm. Diameter: About 4 mm. Angle: About 45° from lateral branch axis. Strength: Flexible, bending with the weight of the flowers. Texture: Sparsely pubescent. Color: Close to 148A.

*Reproductive organs*.—Stamens (present on male flowers only): Quantity per flower: About 50. Filament length: About 4 mm. Filament color: Close to 22B. Anther shape: Obovate; basifixed. Anther length: About 1.5 mm. Anther color: Close to 22A. Pollen amount: Moderate. Pollen color: Close to 11C. Pistils (present on female flowers only): Quantity per flower: About six, fused in pairs. Style length: About 1 cm. Style color: Close to 28B to 28C. Stigma color: Close to 22A. Ovary color: Close to 146B to 146C and 42D.

*Seeds and fruits*.—Seed and fruit development have not been observed on plants of the new *Begonia*.

Disease & pest resistance: Resistance to pathogens and pests common to *Begonia* plants has not been observed on plants of the new *Begonia*.

Garden performance: Plants of the new *Begonia* have been observed to have excellent garden performance, to tolerate high temperatures of about 35° C. and to be hardy to USDA Hardiness Zone 10.

It is claimed:

1. A new and distinct *Begonia* plant named 'KROUTOR01' as illustrated and described.

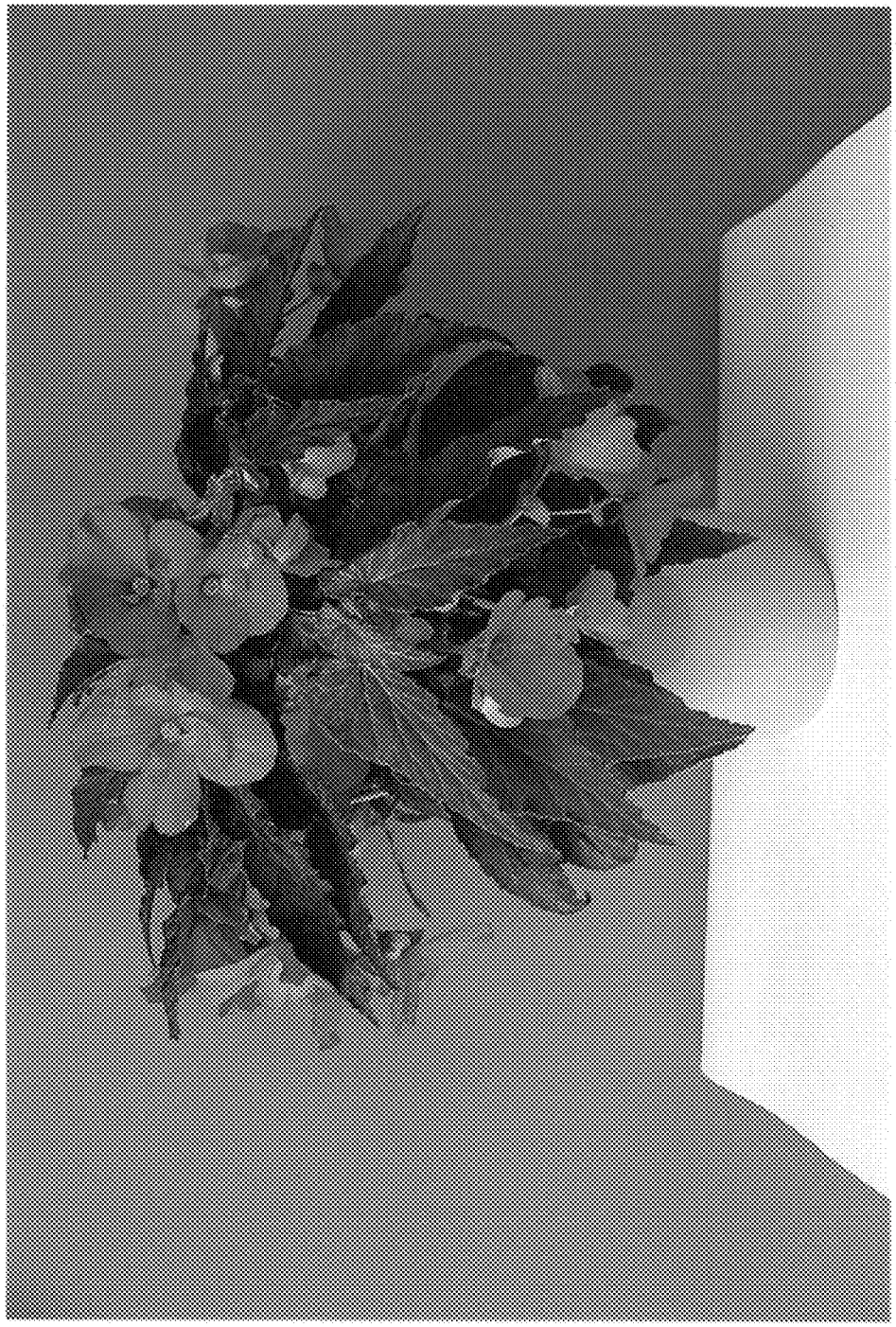

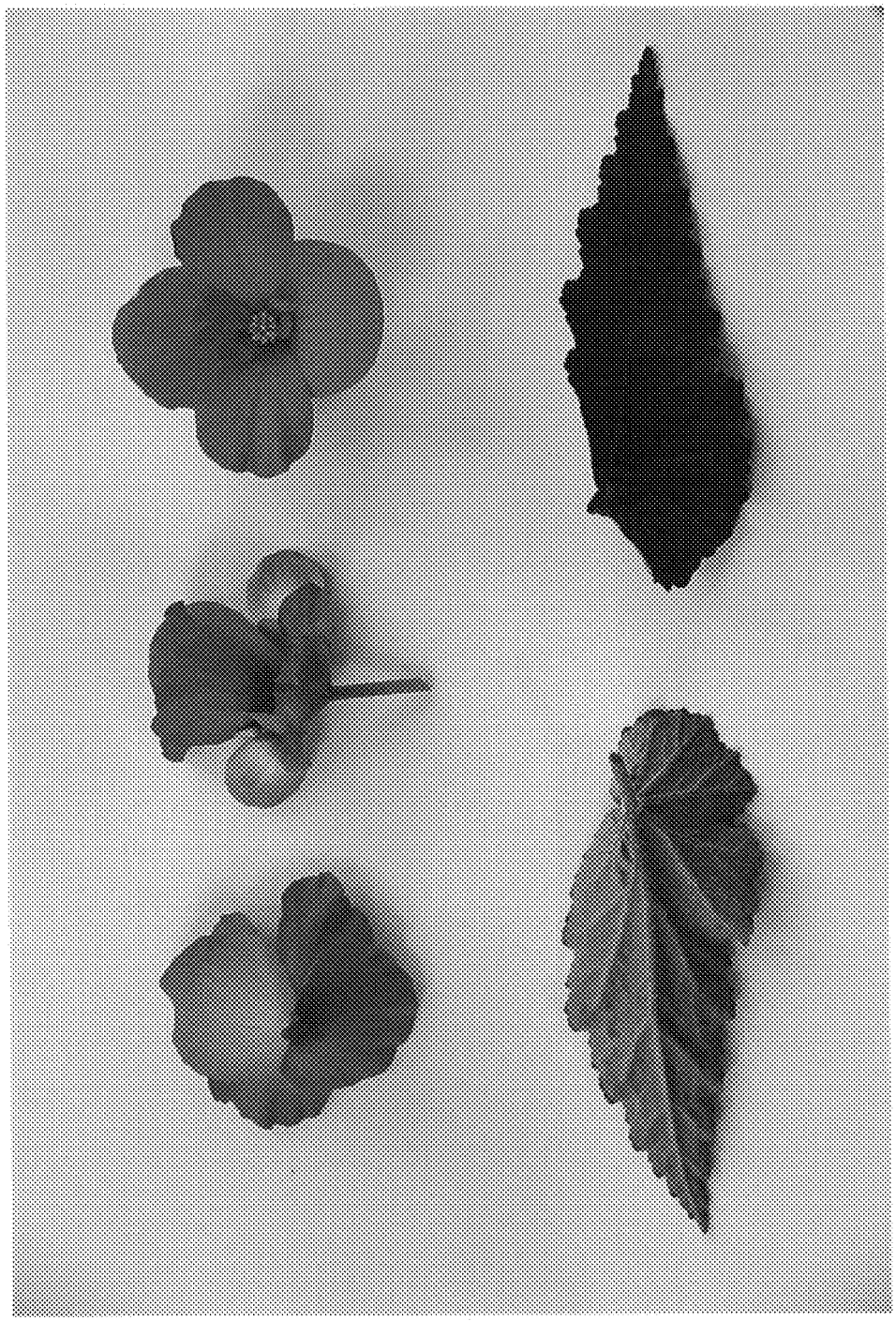

* * * * *